United States Patent [19]

Papanu et al.

[11] 4,372,943

[45] Feb. 8, 1983

[54] NOVEL PESTICIDAL FORMULATION

[75] Inventors: Steven C. Papanu; Ralston Curtis, both of Los Altos, Calif.

[73] Assignee: Zoecon Corporation, Palo Alto, Calif.

[21] Appl. No.: 325,955

[22] Filed: Nov. 30, 1981

Related U.S. Application Data

[63] Continuation-in-part of Ser. No. 228,419, Jan. 26, 1981, abandoned.

[51] Int. Cl.$^3$ .................... A61K 31/74; A01N 25/22; A01N 37/34
[52] U.S. Cl. .................... 424/78; 424/173; 424/304
[58] Field of Search .................... 424/78, 173, 304

[56] References Cited

U.S. PATENT DOCUMENTS

| | | | |
|---|---|---|---|
| 3,399,991 | 9/1968 | Littler | 424/173 |
| 4,243,819 | 1/1981 | Henrick et al. | 424/304 |
| 4,260,633 | 4/1981 | Anderson et al. | 424/304 |

FOREIGN PATENT DOCUMENTS 2025770  1/1980  United Kingdom ............... 424/304

*Primary Examiner*—Delbert R. Phillips
*Assistant Examiner*—F. T. Moezie
*Attorney, Agent, or Firm*—Donald W. Erickson; Jacqueline S. Larson; William B. Walker

[57] ABSTRACT

An oil-in-water pesticidal emulsion concentrate comprising α-cyano-3-phenoxybenzyl-2-(2-chloro-4-trifluoromethylphenylamino)-3-methylbutanoate, polyvinyl alcohol and optional amounts of surfactant and ethylene or propylene glycol having freeze-thaw stability, 50 degrees centigrade stability and water dispersability.

10 Claims, No Drawings

NOVEL PESTICIDAL FORMULATION

CROSS-REFERENCE TO RELATED APPLICATIONS

This is a continuation-in-part of Ser. No. 228,419 filed on Jan. 26, 1981.

BACKGROUND OF THE INVENTION

1. Field of the Invention

This invention relates to novel pesticidal oil-in-water emulsions containing as the active ingredient, α-cyano-3-phenoxybenzyl 2-(2-chloro-4-trifluoromethylphenylamino)-3-methylbutanoate, the preparation thereof and the use of said emulsions for the control of pests.

2. Description of the Prior Art

The compound α-cyano-3-phenoxybenzyl 2-(2-chloro-4-trifluoromethylphenylamino)-3-methylbutanoate has been described by Henrick and Garcia, U.S. Pat. No. 4,243,819 as being an effective agent for the control of pests such as insects and acarids acting in a manner of a synthetic pyrethoid.

Aqueous suspensions of solid pesticide particles having a size of from 5 to 10 microns and containing polyvinyl alcohol, ethylene or propylene glycol, and as an essential ingredient, a thickener such as methyl cellulose, are disclosed in a U.S. Pat. No. 3,399,991. The suspension of solid particles is achieved only in a mixture containing a thickening agent.

U.S. Pat. No. 4,283,415 discloses an oil-in-water pesticidal emulsion having emulsified liquid particles of from 1 to 200 microns in size, polyvinyl alcohol or gum arabic, and a thickener. Suspension stability is achieved only in a viscous mixture containing a thickener.

SUMMARY OF THE INVENTION

The emulsion concentrates of this invention are stable, aqueous oil-in-water dispersions having freeze-thaw stability, 50 degrees centigrade storage stability and disperse readily when diluted with water for application. One embodiment of the composition of this invention comprises a stable pesticidal oil-in-water emulsion concentrate consisting essentially of;

(a) 1 to 50 percent by weight of α-cyano-3-phenoxybenzyl 2-(2-chloro-4-trifluoromethylphenylamino)-3-methylbutanoate dispersed as particles having an average size of less than 1 micron;

(b) 2 to 20% by weight of polyvinyl alcohol having a molecular weight of from 2,000 to 125,000 and having from 11 to 28% of its hydroxy groups present as the acetate ester;

(c) The balance being water; and
the emulsion being freeze-thaw stable, 50 degrees centigrade storage stable, and water dispersable.

Another embodiment of this invention comprises a stable pesticidal oil-in-water emulsion concentrate consisting essentially of;

(a) 1 to 50% by weight of α-cyano-3-phenoxybenzyl 2-(2-chloro-4-trifluoromethylphenylamino)-3-methylbutanoate dispersed as particles having a average size less than 1 micron;

(b) 2 to 20% by weight of polyvinyl alcohol having a molecular weight of from 2,000 to 125,000 and having from 11 to 28% of its hydroxy groups present as the acetate ester;

(c) 0 to 8% by weight of a surfactant selected from the group consisting of anionic surfactants, non-ionic surfactants, amphoteric surfactants, cationic surfactants and mixtures thereof;

(d) 0.1 to 20% by weight of a member selected from the group consisting of ethylene glycol, propylene glycol and mixtures thereof;

(e) The balance being water; and
the emulsion being freeze-thaw stable, 50 degrees centigrade storage stable, and water dispersable.

Because α-cyano-3-phenoxybenzyl 2-(2-chloro-4-trifluoromethylphenylamino)-3-methylbutanoate in its usual form is a thick oily compound at normal ambient temperature, it is desirable as a matter of convenience and practicality to formulate the compound into a more easily handled form.

The conventionally used type of liquid pesticidal formulation, an emulsifiable concentrate (EC), contains as its major ingredient a large amount of an organic solvent. Drawbacks of this formulation, due to the oganic solvent therein, include phytotoxicity to plants, eye and skin irritation to humans and animals, flammability, and the like. The EC formulation also is very sensitive to extremes in water temperature and water hardness.

For these reasons, the aqueous, organic solvent-free formulation of the present invention has been developed. This emulsion exhibits a pesticidal activity equivalent to or exceeding that of a conventional EC formulation. It is freeze-thaw stable, 50 degrees centigrade storage stable and dispersable in water. Furthermore, it is much less irritating to skin and eyes, non-flammable and shows no phytotoxicity. The formulation of this invention can be diluted in water without difficulty in temperature extremes and in either soft water or water having up to 20,000 ppm hardness. To do this is very difficult or impossible with an EC formulation.

DETAILED DESCRIPTION OF THE INVENTION

The pesticidially active compound in the composition of this invention is α-cyano-3-phenoxybenzyl-2-(2-chloro-4-trifluoromethylphenylamino)-3-methylbutanoate. This compound has been described in U.S. Pat. No. 4,243,819. This compound can be prepared as a racemic mixture of four diastereomeric esters or the specific diastereomers as described in U.S. Pat. No. 4,260,633. The compound is normally a thick, viscous oil, and after some prolonged standing of the racemic mixture at certain temperatures, minor crystal growth may occur. The preferred isomer is (S)-α-cyano-3-phenoxybenzyl (R)-2-(2-chloro-4-trifluoromethylphenylamino)-3-methylbutanoate.

In the composition of this invention, the active ingredient must be dispersed as liquid particles having an average size of less than 1 micron. Minimum growth in particle size during a prolonged storage in critical. Therefore, an effective, stable emulsion is critical to the composition of this invention. The present invention includes the use of each of the optical isomers and the racemic mixtures. In the examples, unless otherwise specified, the compound used is the racemic mixture. The concentration of active ingredient is from 1 to 50 weight percent in the dispersion concentrate of this invention.

The composition of this invention contains from 2 to 20 weight percent and preferably from 4 to 6.5 weight percent polyvinyl alcohol. Polyvinyl alcohol suitable for use in composition of this invention has a molecular weight of from 2,000 to 125,000 and is about 72 to 89 mole percent hydrolyzed, that is, has from 11 to 28 percent of its hydroxy groups present in the acetate ester form. One such alcohol is Gelvatol 20/90 (Monsanto), which is 88.7–85.5 mole percent hydrolyzed and has an average molecular weight of 125,000. Another is Gelvatol 40/10, which is 77–72.9 mole percent hydrolyzed and has an average molecular weight of 2,000 or over. A third is Gelvatol 20/30, which is 89–87.7 mole percent hydrolyzed and has an average molecular weight of about 10,000. In contrast, a completely hydrolized polyvinyl alcohol, such as Elvanol (Dupont, less than 1 percent residual polyvinyl acetate), causes failure of the mixture to emulsify.

U.K. Patent Application No. GB 2,025,770 A teaches that gum arabic may be used in place of polyvinyl alcohol in its formulation work. However, in the formulation of the present invention, the mixture proves to be unstable when gum arabic is used.

The composition of this invention contains from 0 to 8 weight percent surfactant. If the embodiments of this invention contain surfactant, the composition should contain from 0.1 to 8 and preferably from 0.25 to 1.0 weight percent surfactant. The surfactants suitable for use in the composition of this invention include anionic, non-ionic and amphoteric surfactants, cationic surfactants and mixtures thereof. Surfactants suitable for use in the formulation of the present invention are, for example, blended surfactants which are designed by the manufacturer specifically for use in emulsifiable concentrates of synthetic organic pesticides. These surfactants are believed to be blends of common anionic and non-ionic surfactants with the most functionally significant component being a calcium aralkyl sulfonate, such as calcium dodecylbenzene sulfonate. Their use in this invention is a novel application not intended by the manufacturer. Such a surfactant may be chosen from, for example, Toximol D (Stepan Chemical); Triton AG-180, AG-190, or AG-193 (Rohm and Haas); the Atlox series (Imperial Chemical Industries); and the Sponto series (Witco).

Another class of surfactants suitable for use in the formulation of the present invention are sodium naphthalene formaldehyde condensates. Examples of such surfactants are Petro Dispersant 425 (Petro Chemicals Co., Inc.), Blancol N (GAF) and Tamol N (Rohm and Haas). Non-ionic surfactants suitable for use in the composition in this invention include surfactants such as Triton CF-21 (Rohm and Haas), a modified ethoxylated non-ionic surfactant. Amphoteric surfactants such as cocoamido betaine (Deriphat Bau, Henkel Corporation) and dodecyl betaine and cocobetaine (Lonzaine 10S and 12C, Lonza, Inc.) can be used in the composition of this invention.

Cationic surfactants, while presenting possible compatibility problems if the composition is to be mixed with anionic containing compositions in the spray tank, is also suitable for use in the composition of this invention when such compatibility problems will not be present. Examples of preferred cationic surfactants are the tertiary amine ethylene oxide condensation products of the primary fatty amines, particularly the tallow and coco acid amines (Ethomeen C-15, Armac Inc.).

The preferred surfactants are the anionic surfactants.

The composition of this invention is freeze-thaw stable and 50 degrees centigrade storage stable. The freeze-thaw stabilizers which are suitable for use in the composition of this invention are propylene glycol, ethylene glycol and mixtures thereof. The concentration of freeze-thaw stabilizer in the composition of this invention is form 0 to 20 and preferably from 5 to 10 weight percent. In one embodiment of this invention containing no surfactant, a freeze-thaw stabilizer is not critical for the composition is freeze-thaw stable without it. However, if surfactant is present in the composition, a freeze-thaw stabilizer is critically necessary to provide a stable formulation.

The emulsions of the present invention can be prepared by dispersing liquid particles of the active ingredient by mechanical means, with or without a surfactant, in an aqueous mixture of polyvinyl alcohol and water and with or without an antifreeze, depending upon the embodiment involved. Thus, the active ingredient is first premixed until uniform with a surfactant if surfactant is included. This mixture is added to the aqueous mixture in a conventional stirrer such as a Waring Blendor, a Sorvall Omni-Mixer or a Kraft Apparatus non-aerating stirrer, usually at a high speed and with heating to a temperature of from 60 to 70 degrees centigrade. In the stirrer, the active ingredient is dispersed in the aqueous phase as liquid particles. Stirring with heating is continued for about 10 to 20 minutes, that is until the particle size average is less than one micron and all individual particles are less than 2 and preferably less than one micron in diameter. The resulting formulation is freeze-thaw stable, 50 degrees centigrade storage stable and dispersable in water. When a surfactant is used to facilitate dispersion of the active ingredient, it is critical that a freeze-thaw stabilizer be present in the formulation. When a surfactant is not used, the freeze-thaw stabilizer is necessary if storage at very low environmental temperatures would be expected.

Prior to this invention, pesticidal emulsions have required thickeners to maintain stability. In the compositions of the present invention, a thickener is not needed for stability. The elimination of the thickener not only saves in cost by material and processing steps, but it provides a dispersable formulation.

The formulation of the present invention is a concentrate of the pesticidally active component. Before normal use, this concentrate is diluted with water to a concentration providing from 0.01 to 0.1 weight percent of the active ingredient. Therefore, the ability of the composition to disperse easily in water is critical. α-cyano-3-phenoxybenzyl 2-(2-chloro-4-trifluoromethylphenylamino)-3-methylbutanoate is a highly active pesticide, particularly against insects and acarids. Among the pests against which the compound is pesticidally effective are insects of the order Lepidoptera, Orthoptera, Heteroptera, Homoptera, Doptera, Coleoptera or Hymenoptera, and acarids of the order Acarina, including mites of the family Tetranychidae or Tarsonemidae and ticks such as Ornithodoros. In the use of the formulation of the present invention for combating insects and acarids, the formulation is applied to the locus in a pesticidally effective amount.

The term "freeze-thaw stable" as used herein with reference to oil-in-water emulsions is defined to mean the respective emulsion has passed the Freeze-Thaw Cycle Test. This test is as follows:

Freeze-Thaw Cycle Test (1) A 5 to 10 ml sample of emulsion is placed in a 10 ml screw-top glass vial and capped.
(2) The vial is placed in a freezing compartment for 16 hours at 15 degrees centigrade. It is then removed and allowed to sit at 24 degrees centigrade for 8 hours.

(3) Repeat Step 2 twice more (to give a total of 3 cycles).

(4) Examine the emulsion. The sample must show no visual signs of oiling (separation of the oil component) or solidification. The sample should move and flow as freely with minimal hand stirring as it did before the test. Unless all of these requirements are satisfied, the emulsion is not freeze-thaw stable.

The term "50 degrees centigrade storage stable" as used herein with reference to oil-in-water emulsions is defined to mean the respective emulsion has passed the 50 Degrees Centigrade Storage Test. This test is as follows:

50 Degrees Centigrade Storage Test (1) A 50 g sample of the emulsion is stored at 50 degrees centigrade in a capped glass vial or other sealed container.

(2) The particle size of this sample is checked at the end of a 30 day period.
  (a) In this procedure, the sample is shaken and one drop (from a pipette) is added to 5 ml deionized water and shaken until homogeneous.
  (b) Two drops of this dispersed sample are placed on a microscope slide and covered with a cover glass.
  (c) Examine slide with a microscope using an oil-immersion lens under 1000× magnification.
  (d) Count number of particles (droplets) having diameter greater than 10 microns in a 18 mm square viewing area. If not more than 10 particles are observed having diameters greater than 10 microns, the test is passed.

The following examples are provided to illustrate the practice of the present invention. Temperature is given in degrees Centigrade. Percentages are percent by weight. The examples set forth procedures actually carried out unless stated to the contrary.

EXAMPLE 1

25.4 grams of technical (88% active) α-cyano-3-phenoxybenzyl 2-(2-chloro-4-trifluoromethylphenylamino)-3-methylbutanoate (also known as "fluvalinate") were premixed with 0.5 g of Toximol D at 60 degrees until uniform. This oil phase was then emulsified into an aqueous phase containing of 5 g of Gelvatol 20/90, 8 g of propylene glycol and 61.1 g. of deionized water by stirring, in a commercial mixer, at maximum rpm, for 15 minutes at 65 degrees. The resulting oil phase particles of the oil-in-water folwable emulsion were all less than 1 micron in diameter, as determined by microscopic inspection.

EXAMPLE 2

A. To an aqueous phase consisting of 5.1% of Gelvatol 20/90, 12.8% of propylene glycol and 57.0% of deionized water was added 25.1% of technical fluvalinate. The mixture was stirred at maximum speed for approximately 10 minutes at 65 degrees. The emulsion was then cooled to room temperature with continued stirring at low speed during the cool-down. The resulting emulsion particles were all less than 2 microns in diameter.

B. Following the above procedure, a flowable emulsion was made by combining 24.9% of fluvalinate with 10.3% of Gelvatol 20/30, 10.0% of propylene glycol and 54.8% of deionized water.

C. In the same manner, 25.4% of fluvalinate was added to 4.8% of Gelvatol 20/90 and 69.8% of dionized water to prepare a flowable emulsion.

EXAMPLE 3

A. Following the procedure of Example 1, an oil-in-water emulsion was prepared by mixing together 12.0% of fluvalinate and 0.5% of Toximol D and then combining the mixture with 5.0% of Gelvatol 20/90, 8.0% of propylene glycol and 74.5% of deionized water.

B. In the same manner, 25.4% of fluvalinate and 1.0% of Toximol D were added to 4.8% of Gelvatol 20/90, 4.8% of propylene glycol and 64.0% of deionized water to make a flowable emulsion.

EXAMPLE 4

Following the method of Example 1, an emulsion was prepared by adding 24.8% of fluvalinate and 8.0% of Triton CF-21 to 5.1% of deionized water. The resulting oil phase particles of the emulsion were all less than 1 micron in diameter.

EXAMPLE 5

Following Example 1 procedures, 40.0% of fluvalinate and 0.5% of Toximol D were added to 30.0% of Gelvatol 40/10, 8.0% of ethylene glycol and 21.5% of deionized water to prepare an emulsion. The foregoing percentages are percent by weight of the total premix weight. This premix was then diluted with deionized water to a final concentration of 24.8% of fluvalinate.

EXAMPLE 6

Following the procedure of Example 1, a mixture of 23.54% of fluvalinate and 0.54% of Petro 425 dispersant was added to 8.25% of Gelvatol 20/30, 8.00% of ethylene glycol and 59.6% of deionized water to prepare an oil-in-water emulsion.

What is claimed is:

1. A stable pesticidal oil-in-water concentrate free from thickeners and consisting essentially of:
  (a) 1 to 50% by weight of α-cyano-3-phenoxybenzyl 2-(2-chloro-4-trifluoromethylphenylamino)-3-methylbutanoate dispersed as particles having an average size less than 1 micron;
  (b) 2 to 20% by weight of polyvinyl alcohol having a molecular weight of from 2,000 to 125,000 and having from 11 to 28% of its hydroxy groups present as the acetate ester;
  (c) the balance being water; and
the emulsion being freeze-thaw stable, 50 degrees Centigrade storage stable and water dispersable.

2. The dispersion concentrate of claim 1 wherein concentration of polyvinyl alcohol is from 4 to 6.5% by weight.

3. A pesticidal composition comprising the dispersion concentrate of claim 1 diluted with sufficient water to provide a concentration of from 0.01 to 0.1 weight percent of α-cyano-3-phenoxybenzyl 2-(2-chloro-4-trifluoromethylphenylamino)-3-methylbutanoate.

4. A method for combatting insects and acarids which comprises applying the composition of claim 3 to the locus in a pesticidally effective amount.

5. The composition of claim 1 containing as the active ingredient, (S)-α-cyano-3-phenoxybenzyl (R)-2-(2-chloro-4-trifluoromethylphenylamino)-3-methylbutanoate.

6. A stable pesticidal dispersion concentrate free from thickeners and consisting essentially of:

(a) 1 to 50% by weight by α-cyano-3-phenoxybenzyl 2-(2-chloro-4-trifluoromethylphenylamino)-3-methylbutanoate dispersed as particles having an average size less than 1 micron;

(b) 2 to 20% by weight of polyvinyl alcohol having a molecular weight of from 2,000 to 125,000 and having from 11 to 28% of its hydroxy groups present as the acetate ester;

(c) 0 to 8% by weight of surfactant selected from the group consisting of anionic surfactants, non-ionic surfactants, amphoteric surfactants, cationic surfactants and mixtures thereof;

(d) 0.1 to 20% by weight of a member selected from the group of freeze-thaw stabilizers consisting of ethylene glycol, propylene glycol and mixtures thereof;

(e) the balance being water; and the emulsion being freeze-thaw stable, 50 degrees Centigrade storage stable and water dispersable.

7. The dispersion concentrate of claim 6 wherein the surfactant concentration if from 0.1 to 8% by weight and the concentration of freeze-thaw stabilizer is from 5 to 10% by weight.

8. A pesticidal composition comprising the dispersion concentrate of claim 6 diluted with sufficient water to provide a concentration of from 0.01 to 0.1 weight percent of α-cyano-3-phenoxybenzyl 2-(2-chloro-4-trifluoromethylphenylamino)-3-methylbutanoate.

9. The method for combatting insects and acarids which comprises applying the composition of claim 8 to the locus in a pesticidally effective amount.

10. The composition of claim 6 containing as the active ingredient, (S)-α-cyano-3-phenoxybenzyl (R)-2-(2-chloro-4-trifluoromethylphenylamino)-3-methylbutanoate.

* * * * *